United States Patent
Lee et al.

(10) Patent No.: US 11,643,688 B2
(45) Date of Patent: May 9, 2023

(54) METHOD FOR DIAGNOSING MOOD DISORDER BY USING CIRCADIAN RHYTHM

(71) Applicant: HUCIRCADIAN CO., LTD., Seoul (KR)

(72) Inventors: Heon-Jeong Lee, Seoul (KR); Chul-Hyun Cho, Seoul (KR); Joung-Ho Moon, Gyeonggi-do (KR)

(73) Assignee: HUCIRCADIAN CO., LTD., Seoul (KR)

( * ) Notice: Subject to any disclaimer, the term of this patent is extended or adjusted under 35 U.S.C. 154(b) by 512 days.

(21) Appl. No.: 16/469,760

(22) PCT Filed: Feb. 13, 2017

(86) PCT No.: PCT/KR2017/001541
§ 371 (c)(1),
(2) Date: Jun. 14, 2019

(87) PCT Pub. No.: WO2018/110766
PCT Pub. Date: Jun. 21, 2018

(65) Prior Publication Data
US 2020/0080151 A1    Mar. 12, 2020

(30) Foreign Application Priority Data
Dec. 15, 2016    (KR) .......................... 10-2016-0171816

(51) Int. Cl.
*C12Q 1/6883* (2018.01)
*G01N 33/74* (2006.01)

(52) U.S. Cl.
CPC ......... *C12Q 1/6883* (2013.01); *G01N 33/743* (2013.01); *C12Q 2600/112* (2013.01); *C12Q 2600/158* (2013.01); *G01N 2333/575* (2013.01)

(58) Field of Classification Search
None
See application file for complete search history.

(56) References Cited

U.S. PATENT DOCUMENTS

2011/0092377 A1    4/2011    Agrawal et al.

FOREIGN PATENT DOCUMENTS

JP    2013216628    10/2013

OTHER PUBLICATIONS

Li (PNAS Jun. 11, 2013 vol. 110 No. 24 pp. 9950-9955).*
Novakova (Bipolar Disord May 2015; 17(3) pp. 303-314).*
Moon (EbioMedicine 11 (2016) pp. 285-295, pub online Aug. 13, 2016).*
Milhiet (Frontiers in Bioscience S6 120-137 Jan. 2014).*
Dallaspezia (Curr Psychiatry Rep 2015 vol. 17 No. 68).*
Cho (Scientific Reports 6:31846 Pub Aug. 22, 2016).*
Cho et al., "Molecular Circadian Rhythm Shift Due to Bright Light Exposure Before Bedtime is Related to Subthreshold Biolarity", Scientific Reports, vol. 6, Doc. No. 31846, Aug. 22, 2016, pp. 1-13.
Simons et al., "Development of the Cortisol Circadian Rhythm in the Light of Stress Early in Life", Psychoneuroendocrinology, vol. 62, 2015, pp. 292-300.
Moon et al., "Advanced Circadian Phase in Mania and Delayed Circadian Phase in Mixed Mania and Depression Returned to Normal after Treatment of Bipolar Disorder", EBioMedicine, vol. 11, 2016, pp. 285-295.
The Committee of Nomenclature and Statistics of the American Psychiatric Association, "Diagnostic and Statistical Manual Mental Disorders", American Psychiatric Association, 1952.
Sekula et al., "Neuroendocrine Aspects of Primary Endogenous Depression XV: Mathematical Modeling of Nocturnal Melatonin Secretion in Major Depressives and Normal Controls", Psyychiatry Research, vol. 69, 1997, pp. 143-153.
Maletic et al., "Integrated Neurobiology of Bipolar Disorder", Frontiers in Psychiatry, vol. 5, Aug. 2014, Article 98.
Mansour et al., "Circadian Genes and Bipolar Disorder", Annals of Medicine, vol. 37, 2005, pp. 196-205.

* cited by examiner

*Primary Examiner* — Amanda Haney
(74) *Attorney, Agent, or Firm* — Duane Morris LLP; Gregory M. Lefkowitz; Brandon A. Chan

(57) ABSTRACT

The present disclosure relates to a method for diagnosing mood disorder such as mania, depression and mania mixed using a circadian rhythm. According to the diagnostic method of the present disclosure, the condition of mood disorder can be diagnosed objectively and clearly based on the advance or delay of the circadian rhythm. That is to say, hypomania, mania, depression, mixed mania, etc. may be determined quickly and adequately so that appropriate therapeutic intervention can be made. In addition, according to the diagnostic method of the present disclosure, schizophrenia which is frequently confused with severe depression or bipolar disorder can be distinguished clearly. In addition, the selection of a therapeutic drug can be benefited greatly through this.

6 Claims, 12 Drawing Sheets

Specification includes a Sequence Listing.

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctcacacagc tcctcctcag                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttgtgctct tgctgctctc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cggcaaggac tcagccctgc                                              20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgcctcgtcg caattgg                                                 17

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 5
accctgattt ccccgttca                                                    19

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgactgcatt ctcatgtagt tccacaacca                                        30
```

METHOD FOR DIAGNOSING MOOD DISORDER BY USING CIRCADIAN RHYTHM

CROSS-REFERENCE TO RELATED APPLICATIONS

This application is a § 371 national stage entry of International Application No. PCT/KR2017/001541, filed on Feb. 13, 2017, which claims priority to Korean Patent Application No. 10-2016-0171816, filed Dec. 15, 2016, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 31, 2023, is named H3655-00101_SL.txt and is 1,747 bytes in size.

TECHNICAL FIELD

The present disclosure relates to a method for diagnosing mood disorder such as mania, depression, mixed mania, etc. using a circadian rhythm.

BACKGROUND ART

At present, because psychiatric diagnosis is made based on symptoms, the diagnosis results are often different from clinicians to clinicians, and it is not uncommon that the diagnosis is changed during treatment.

The psychiatric community has been pondering on how to ensure objectivity in the diagnosis of mental disorder. Schizophrenia cannot be diagnosed with diagnostic imaging tools such as CT scanning or MRI, and depression cannot be diagnosed with biopsy. Although a number of physiological diagnostic tests have been attempted, no reliable result has been achieved yet. Only 60 years ago, the diagnosis result on a patient varied significantly depending on where the psychiatrist received training, which patients he/she had treated mainly and what he/she was from. Aside from the difference between the East and the West, there was difference even between American and British doctors. In 1940s, an experiment was conducted wherein doctors in the United States and the United Kingdom were shown images of a patient and were asked to make diagnosis. The patient was a young male with a history of alcohol abuse and showing rapid change in sentiment, with paralysis on one arm. Whereas 69% of the 46 American psychiatrists diagnosed the patient as having schizophrenia, only 2% of the 205 British psychiatrists made the same diagnosis.

A common diagnostic system that can be used by psychiatrists was required to resolve this confusion of mental disorder diagnosis, and the social consensus that a system is necessary to accurately represent symptoms and to make a specific diagnosis when the symptoms are maintained above certain levels for a certain period of time began to spread.

In this regard, the American Psychiatric Association published the "Diagnostic and Statistical Manual of Mental Disorders (DSM)" in 1952. The intent of the association was to ensure the objectivity, systemicity and accuracy of a diagnostic system as much as possible so that anyone who has received appropriate training, even if he/she is not an expert, can make diagnosis based on the system.

The 3rd edition of the DSM, which was published in 1980 through a number of modifications and amendments, finally reached a level enough to say that it is based on the traditional medical model and became the basis to be incorporated into the mainstream medical diagnostic systems. It was a great advantage that experienced doctors could provide highly congruent diagnosis and specifically describe objective symptoms in a quantitative manner. Thanks to the official guideline that can be easily consulted by anyone, the diagnostic criteria began to spread quickly not only to mental hospitals but also to health institutions, social welfare institutions, private insurance companies, courts, prisons, universities, etc. The insurance companies referred to the DSM for adequate diagnoses for payment of benefits to patients, and lawyers began to cite the diagnostic criteria of the DSM to appeal to the judges and jury that their clients have mental illness. As a result, the 3rd edition of the DSM spread worldwide beyond the United States. In Korea, the DSM began to be used as the primary diagnostic criteria rather than the International Classification of Diseases around this time. Although the International Classification of Diseases (ICD) established by the World Health Organization (WHO) is a basic diagnostic tool all over the world, the DSM takes priority regarding mental disorders. The DSM, which now is considered as a standard worldwide beyond the United States and is cited for every case, is called "the psychiatry's bible". In 2013, the American Psychiatric Association published the 5th edition of the DSM after years of preparation, wherein obsessive-compulsive disorder and trauma/stress-associated disorders are treated as new categories.

However, the diagnostic criteria of the DSM have been criticized that they are merely a collection of clinical symptoms and have not been verified through objective laboratory evaluations (medical imaging, blood tests, neurophysiological tests, etc.). It is because the diagnostic criteria of the DSM are dependent on the subjective judgment of the evaluators, and the diagnosis results often vary depending on the subjective statements of the patients or caregivers.

At present, the market of mood disorder-related diseases such as depression, bipolar disorder (also known as manic depression), etc. is fairly large. For modern people, the lifetime prevalence of depression is about 15%, and the lifetime prevalence of bipolar disorder is about 5%. The economic cost resulting therefrom is considered to be astronomical. For the moderners who suffer from severe disturbance of life rhythms and stresses, these psychiatric disorders are increasing gradually.

Accordingly, the development of a diagnostic method capable of replacing or supplementing the diagnostic criteria of the DSM, which are highly dependent on the subjective judgment of the evaluators, is necessary to objectively and easily evaluate mania, depression or mixed conditions by using a circadian rhythm (endogenous biorhythm).

DISCLOSURE

Technical Problem

The present disclosure is directed to providing a method for specifically diagnosing mood disorder conditions such as mania, depression, mixed mania, etc. using a circadian rhythm. In addition, the present disclosure is directed to providing a method for distinguishing mood disorder and schizophrenia, the psychotic symptoms of which can be confused easily in the acute phase.

Technical Solution

Therefore, the present disclosure provides a diagnostic method of mood disorder using a circadian rhythm, which includes a step of determining the change in an endogenous factor during a period when the phase variation of a circadian rhythm can be determined.

The mood disorder may be one selected from a group consisting of mania, depression and mixed mania.

In addition, the endogenous factor may be cortisol.

In addition, the endogenous factor may be the PER1 gene and the ARNTL gene, and the circadian rhythm may be embodied by calculating the ratio of the expression levels of the PER1 gene and the ARNTL gene.

The change in the endogenous factor may be measured with an interval of 2-6 hours.

In addition, the present disclosure provides a diagnostic method of mood disorder, which includes: a step of collecting a biological sample from a subject for 24-48 hours with an interval of 2-6 hours and measuring an endogenous factor in the sample; a step of embodying a circadian rhythm by acquiring the measured endogenous factor as time-series data; and a step of comparing the circadian rhythm with the circadian rhythm of a normal person.

In addition, the endogenous factor may be measured except for sleeping hours.

In addition, in the diagnostic method according to an exemplary embodiment of the present disclosure, mood disorder may be diagnosed if the circadian rhythm of a patient showing psychiatric disorder shows a difference of at least 3 hours when compared with that of a normal person.

In addition, in the diagnostic method according to an exemplary embodiment of the present disclosure, mania may be diagnosed if the circadian rhythm is 4-12 hours ahead as compared to that of a normal person, depression may be diagnosed if the circadian rhythm is delayed by 3-6 hours as compared to that of a normal person, and mixed mania may be diagnosed if the circadian rhythm is delayed by 6-12 hours as compared to that of a normal person.

In addition, the present disclosure provides a method for distinguishing mood disorder and schizophrenia, which includes: a step of collecting a biological sample from a subject suspected to have mood disorder or schizophrenia or diagnosed with mood disorder or schizophrenia for 24-48 hours with an interval of 2-6 hours and measuring an endogenous factor in the sample; a step of embodying a circadian rhythm by acquiring the measured endogenous factor as time-series data; and a step of comparing the circadian rhythm with that of a normal person and diagnosing schizophrenia if the difference is less than 2 hours.

In addition, the present disclosure provides a kit for diagnosing mood disorder, which contains 6-15 injection ports for saliva samples provided in a substrate, wherein numbers, letters or symbols are marked on the side of the injection ports so as to sequentially inject the saliva samples to the injection ports for 24-48 hours with an interval of 2-6 hours.

According to the diagnostic method of the present disclosure, the condition of mood disorder can be diagnosed objectively and clearly based on the advance or delay of the circadian rhythm. That is, hypomania, mania, depression, mixed mania, etc. may be determined quickly and adequately so that appropriate therapeutic intervention can be made.

In addition, according to the diagnostic method of the present disclosure, schizophrenia, which is frequently confused with severe bipolar disorder (manic depression), can be clearly distinguished. Through this, the selection of a therapeutic drug can be benefited greatly.

BEST MODE

Figure 1A:
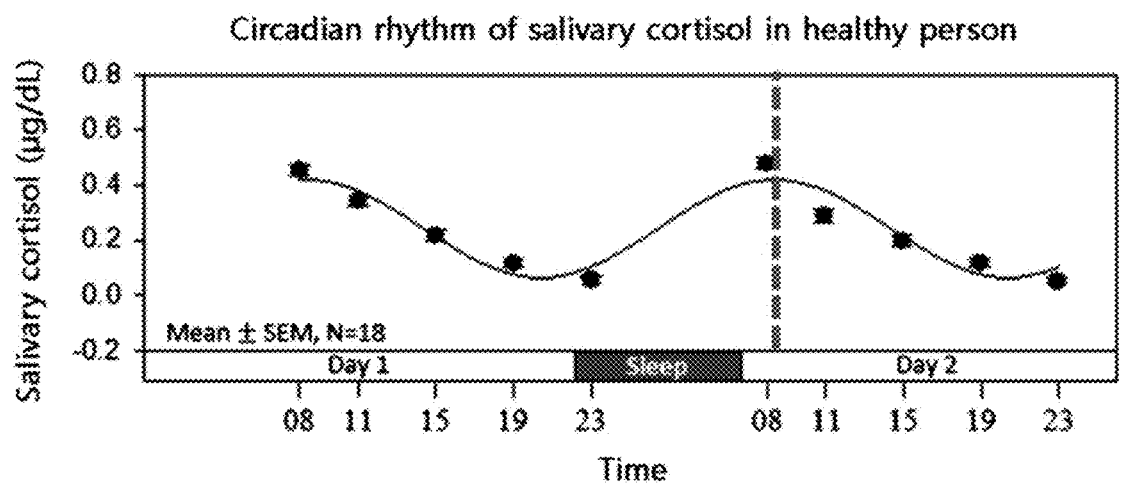
FIG. 1A is a graph showing the circadian rhythm of a normal person embodied by measuring cortisol concentration.

Hereinafter, the present disclosure is described in more detail.

The present disclosure relates to a diagnostic method of mood disorder using a circadian rhythm, which includes a step of determining the change in an endogenous factor during a period when the phase variation of a circadian rhythm can be determined. Specifically, the change of the endogenous factor may be measured with an interval of 2-6 hours.

More specifically, the diagnostic method according to an exemplary embodiment of the present disclosure is a diagnostic method of mood disorder, which includes: a step of collecting a biological sample during a period when the phase variation of a circadian rhythm can be determined, specifically for 24-48 hours, with an interval of 2-6 hours and measuring an endogenous factor in the sample; a step of embodying a circadian rhythm by acquiring the measured endogenous factor as time-series data; and a step of comparing the circadian rhythm with the circadian rhythm of a normal person.

In the specification of the present disclosure, the "circadian rhythm" refers to a biorhythm that repeats with a period of "about a day", i.e., 24 hours. It is also called an endogenous biorhythm. It refers to the period of hormone secretion in human, the period of secretion of neurotransmitters that regulate sleep, the period of mood and energy, etc. The human body regulates its biorhythm and hormone secretion according to the circadian period (the Earth's rotation period). If a person suffers from sleep troubles or change in mood, it is highly likely that it is caused by a problem with the circadian rhythm. In a strict sense, the circadian rhythm is generated endogenously. The circadian rhythm makes the human biorhythm including sleeping hours repeat with a period of 22-25 hours. At night, the body movement is minimized so that organs can rest. In contrast, secretion occurs vigorously during the daytime. At about 9 o'clock at night, as the sleep hormone 'melatonin', which induces sleep, begins to be secreted to induce sleep. And, at 6-8 a.m., the secretion of 'cortisol', a hormone which prepares wake from sleep, reaches the maximum.

In the specification of the present disclosure, the "mood disorder" refers to a mental disorder where extremely depressed or elevated mood is continued, leading to serious difficulties in adapting to real life. It is a condition that occurs due to the abnormality of the region of the brain that regulates mood. Depression, hypomania, mania, mixed mania, major depressive disorder, dysthymic disorder, unclassified-type depressive disorder, type I bipolar disorder, type II bipolar disorder, cyclothymic disorder, etc. belong to mood disorder. It is can be largely classified into depression, mania, mixed mania, etc. depending on the state of mood.

In the specification of the present disclosure, the "PER1/ARNTL genes" means a ratio (value) obtained by dividing the expression level of the PER1 gene by the expression level of the ARNTL gene.

In the specification of the present disclosure, the "acrophase" refers to the time when the circadian rhythm reaches the maximum (peak). Specifically, it means the time when the circadian rhythm expressed by a sinusoid reaches the maximum (peak).

The diagnostic method of mood disorder according to an exemplary embodiment of the present disclosure is a method using the change of a circadian rhythm and includes a step of determining the change in an endogenous factor during a period when the phase variation of a circadian rhythm can be determined. The period when the phase variation of a circadian rhythm can be determined may be specifically 12-56 hours, more specifically 24-48 hours.

More specifically, the diagnostic method according to an exemplary embodiment of the present disclosure includes a step of collecting a biological sample from a subject during a period when the phase variation of a circadian rhythm can be determined, specifically for 12-56 hours with an interval of 12-56 hours, more specifically for 24-48 hours with an interval of 2-6 hours, and measuring an endogenous factor in the sample.

The biological sample may be a sample selected from blood, plasma, serum, saliva, urine, tear, snivel, hair, hair root, and a buccal epithelial cell.

And, specifically, the endogenous factor of the present disclosure may be cortisol. Specifically, when the endogenous factor is cortisol, the biological sample may be saliva. More specifically, the concentration of cortisol may be measured from the saliva of a subject.

In addition, the endogenous factor of the present disclosure may be specifically one or more circadian clock gene selected from a group consisting of ARNTL, PER1, PER2, PER3, NR1D1, NR1D2, CLOCK, CRY1, CRY2 and NPAS2. More specifically, the circadian clock gene may be selected from a group consisting of ARNTL, PER1, PER2, PER3 and NR1D1. The circadian clock genes may embody a circadian rhythm with the expression level of one clock gene selected from the group or with a ratio of the expression levels of two circadian clock genes as a combination.

Most specifically, a combination of the PER1 gene and the ARNTL gene may be used as the endogenous factor of the present disclosure. Most specifically, a circadian rhythm may be embodied with a ratio (value) of the expression level of the PER1 gene divided by and the expression level of the ARNTL gene.

Specifically, when the endogenous factor is a ratio of the expression levels of the PER1 and ARNTL genes, the biological sample may be a buccal epithelial cell. More specifically, after harvesting buccal epithelial cells of a subject and isolating total RNAs from the collected buccal epithelial cells, the isolated RNA sample is subjected to reverse transcription and the resulting cDNA is amplified by real-time PCR (Taqman assay) to measure the ratio of the expression levels of the two genes.

Specifically, the endogenous factor may be measured except for sleeping hours.

Next, the diagnostic method of mood disorder according to an exemplary embodiment of the present disclosure includes a step of embodying a circadian rhythm by acquiring the measured endogenous factor as time-series data.

In the specification of the present disclosure, the "time-series data" refers to data of the concentration of cortisol or the ratio of the expression levels of the PER1 and ARNTL genes arranged in a table according to the collection time of the biological sample of the subject.

And, the diagnostic method of mood disorder according to an exemplary embodiment of the present disclosure includes a step of comparing the circadian rhythm with the circadian rhythm of a normal person. Specifically, mood disorder may be diagnosed if the circadian rhythm shows a difference of at least 3 hours when compared with that of a normal person.

Furthermore, mania or hypomania may be diagnosed if the circadian rhythm is 4-12 hours, more specifically 5-11 hours, ahead as compared to that of a normal person, depression may be diagnosed if the circadian rhythm is delayed by 3-6 hours, more specifically 4-5 hours, as compared to that of a normal person, and mixed mania may be diagnosed if the circadian rhythm is delayed by 6-12 hours, more specifically 7-11 hours, as compared to that of a normal person.

According to the diagnostic method of mood disorder of the present disclosure, mood disorder such as hypomania, mania, depression, mixed mania, etc. can be diagnosed objectively and clearly and schizophrenia, which is frequently confused with severe bipolar disorder, can be distinguished clearly based on the advance or delay of the circadian rhythm.

For example, if a patient has problems of psychiatric symptoms (suspected to have mood disorder or schizophrenia or diagnosed with mood disorder or schizophrenia), the circadian rhythm (endogenous biorhythm) is measured. Then, mood disorder may be diagnosed if there is a change in the circadian rhythm, and schizophrenia may be diagnosed if there is no change in the circadian rhythm.

Hereinafter, the present disclosure will be described in detail through examples. However, the following examples and test examples are for illustrative purposes only and the scope of the present disclosure is not limited by them. The present disclosure can be changed variously within the scope of the technical idea of the present disclosure and such changes are included in the scope of the present disclosure defined by the appended claims.

EXAMPLES

Test Subjects

Test subjects were selected from the patients hospitalized in the Department of Psychiatry of Korea University Anam Hospital. 26 cases of manic episodes that occurred in 22 inpatients (12 male and 10 female) with bipolar disorder (BD-I) from May 2012 until June 2014, and 5 cases of depressive episodes that occurred in 5 inpatients with bipolar disorder (2 male and 3 female, 2 with BD-I and 3 with BD-II) from June 2014 until March 2015 were studied. As a control group, 18 healthy people (11 male and 7 female) were evaluated from September 2012 until November 2012. The age of the patients was 30.42±10.88 years and the age of the healthy control group was 23.00±3.57 years. One of the inpatients was monitored for both bipolar disorder and depressive episode during different hospital stays. In summary, 31 cases of mood episode were analyzed for 26 bipolar disorder patients who required hospitalization. There was no significant difference in age and gender between the groups.

Diagnosis was made by two psychiatrists (H.-J.L and C.-H.C) using the Korean version of the Mini-international neuropsychiatric interview (Yoo et al., 2006) according to the DSM-IV-TR. One bipolar disorder patients had to be hospitalized due to worsening of the symptoms of mood disorder was included in this study. The inclusion criteria of the participants were: 1) diagnosis as bipolar disorder according to the DSM-IV-TR and 2) acute mood disorder episode requiring hospitalization for intensive psychiatric treatment. The patients suffering from intellectual disability, organic brain damage or other major mental disorders or the control group were excluded from the study. All the participants were screened to exclude past or present major diseases such as cardiovascular diseases, metabolic diseases (including diabetes mellitus), hormonal disorders (including thyroid diseases) and cancer.

All the voluntary participants of the control group were verified to have no personal or familial psychiatric history through in-depth interviews by psychiatrists. All the participants filled out a questionnaire on sleep in order to exclude those with irregular or unstable sleep patterns. In addition, those who work on a night shift or show a sleep pattern suggesting circadian rhythm phase disorder were excluded from the control group. The mood disorder questionnaire (MDQ) was used to evaluate subthreshold bipolarity (Hirschfeld et al., 2000), and only those who with MDQ scores below 7 points were included in the control group.

Test Environment and Sampling

The patients were hospitalized during treatment and wore Actiwatch-L activity recorders on the wrist (Philips Respironics, Bend, Oreg., USA). The sleep habits of the hospitalized subjects were controlled by the regular ward routine, i.e., they went to bed at 22:00 h and were awakened at 06:00 h. Light exposure was also controlled by the ward routine, i.e., the lights were turned off from 22:00 h to 06:00 h and turned on from 06:00 h to 22:00 h. All the patients with bipolar disorder had free access to natural light through the windows during the day, and provided saliva samples (1 mL or more) directly into Salivettes (Sarstedt AG & Co., Numbrecht, Germany). Buccal epithelial cells were collected and immediately placed into RNAlater (Sigma-Aldrich, St. Louis, Mo., USA). Sample collection was begun with the start of hospitalization and continued at 08:00, 11:00, 15:00, 19:00, and 23:00 for two consecutive days, and then repeated at two-week intervals during the hospitalization. Nighttime sample collection at 23:00 was performed by well-trained experimental staff without additional light exposure, under light as dim as possible. But, the collection did require brief awakening, and the patients with acute psychiatric illnesses usually had disturbed sleep.

Each control group subject participated in the study for 1 week and wore Actiwatch-L. The controls lived near the hospital and were asked to maintain the same sleep-wake schedule as the hospitalized bipolar disorder patients. They were hospitalized for the last two days of their participation, and sampling was performed under the same conditions as the patients.

Example 1: Diagnostic Method Using Circadian Rhythm (Cortisol)

After preparing samples by taking saliva of patients suspected with mood disorder for two days at 8:00, 11:00, 15:00, 19:00 and 23:00 for a total of 10 times, the concentration of in the samples was measured. Coat-A-Count Cortisol (Siemens Healthcare Diagnostics Inc., Los Angeles, USA) was used for the measurement of the cortisol concentration. The analytical sensitivity was 0.01 µg/dL. The intra-assay coefficient of variation was 3% for samples of 0.19±0.10 µg/dL, and 4% for samples of 0.24±0.02 µg/dL. The inter-assay coefficient of variation was 12% for samples of 1.85±0.10 µg/dL, and for samples of 0.24±0.02 µg/dL.

The measured cortisol concentration was acquired as time-series data and a circadian rhythm was embodied as an optimized sine function. The SigmaPlot software (Systat Software Inc., San Jose, Calif., USA) was used to embody the biological rhythm as a sine curve.

The embodied circadian rhythm of a patient is compared with the circadian rhythm of a normal person shown in FIG. 1A. Mania was diagnosed if the circadian rhythm was 4-12 ahead as compared to a normal person, depression was diagnosed if the circadian rhythm was delayed by 3-6 hours as compared to a normal person, and mixed mania was diagnosed if the circadian rhythm was delayed by 6-12 hours as compared to a normal person.

Then, the patients diagnosed with mood disorder were monitored while treating for 2-4 weeks.

Figure 2A:
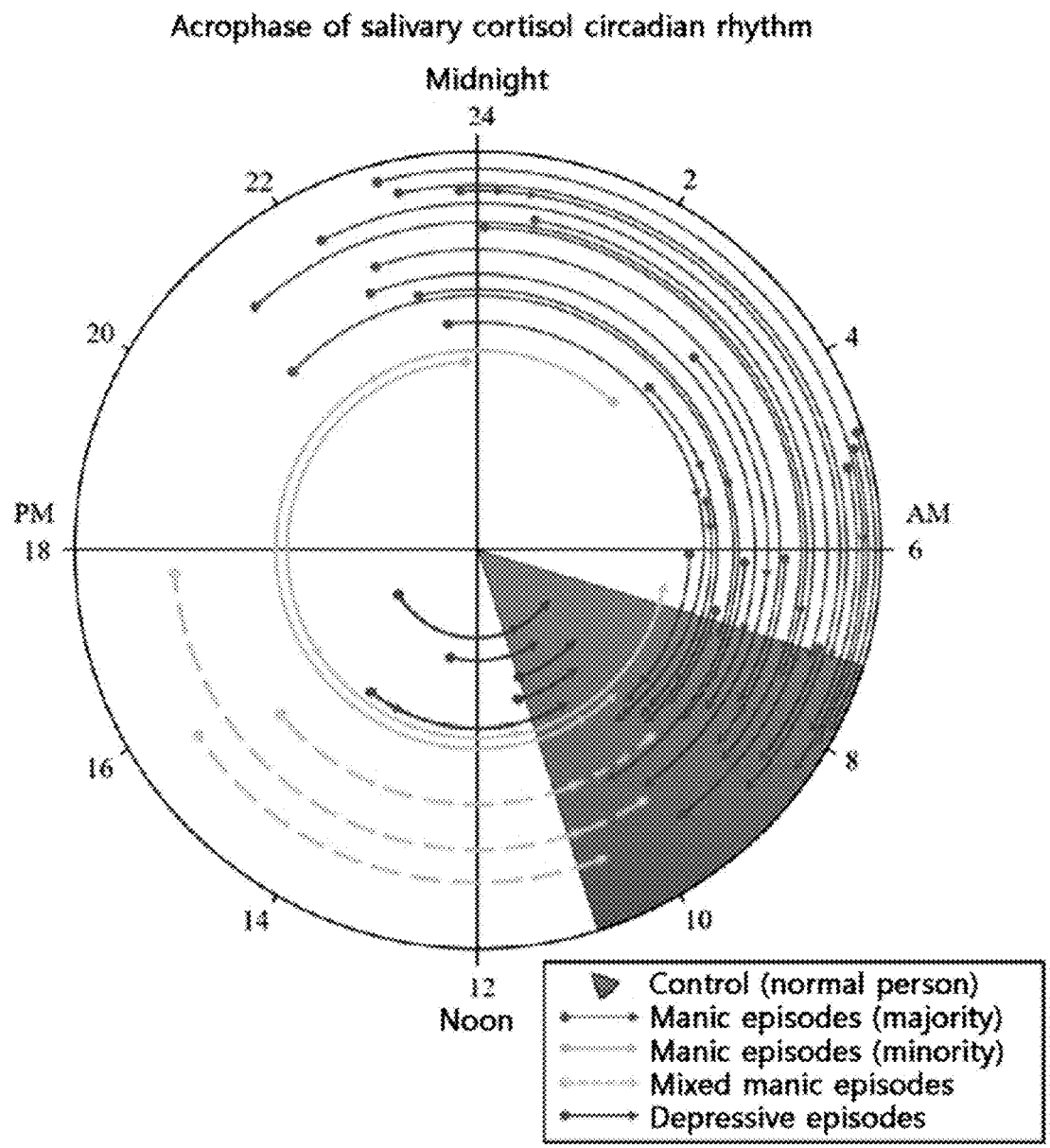
FIG. 2A is a graph showing the change in the acrophase of a biochemical circadian rhythm of cortisol for acute mania and depressive episode during treatment.

FIG. 2A and Tables 1 and 2 clearly show that the biochemical circadian rhythms of the patients with acute mania and depressive episode are different from the biochemical circadian rhythm of a normal person (control group). In particular, as shown in FIG. 2A, although the biochemical circadian rhythms had contrasting initial phases during acute mania and depression, they were transited by comparable phase shifts during recovery, almost entirely arriving within the normal ranges.

TABLE 1

| | Manic episodes (N = 26) | | | | | | | |
|---|---|---|---|---|---|---|---|---|
| | Manic episodes (majority) | | | | Manic episodes (minority) | | | |
| Observation | Mania N = 21 | 2 weeks after N = 16 | 4 weeks after N = 4 | Recovered N = 21 | Mania N = 2 | 2 weeks after N = 2 | 4 weeks after N = 2 | Recovered N = 2 |
| Acrophase (h) | 2.03 ± 3.41 | 6.18 ± 2.13 | 6.61 ± 3.87 | 8.53 ± 0.88 | 0.98 ± 1.7 | 18.37 ± 3.86 | 10.52 ± 0.41 | 7.71 ± 2.12 |
| Amplitude (μg/dL) | 0.19 ± 0.1 | 0.18 ± 0.09 | 0.24 ± 0.07 | 0.21 ± 0.06 | 0.35 ± 0.12 | 0.23 ± 0.1 | 0.18 ± 0.15 | 0.21 ± 0.05 |

N: number of episodes in bipolar disorder patients

TABLE 2

| | Manic episodes (N = 26) Mixed manic episodes | | | Depressive episodes | | | Controls |
|---|---|---|---|---|---|---|---|
| Observation | Mixed N = 3 | 2 weeks after N = 2 | Recovered N = 3 | Depressive N = 5 | 2 weeks after N = 2 | Recovered N = 5 | (normal people) N = 18 |
| Acrophase (h) | 16.34 ± 1.5 | 10.47 ± 0.03 | 9.64 ± 0.88 | 13.83 ± 2.78 | 12.68 ± 2.87 | 9.15 ± 0.72 | 8.44 ± 0.92 |
| Amplitude (μg/dL) | 0.26 ± 0.1 | 0.19 ± 0.04 | 0.23 ± 0.01 | 0.19 ± 0.03 | 0.20 ± 0.03 | 0.19 ± 0.02 | 0.19 ± 0.08 |

N: number of episodes in bipolar disorder patients or number or people in control group (normal)

As shown in Table 1 and Table 2, the circadian rhythm or acrophase of manic patients were 4-12 hours ahead as compared to the normal people. It was delayed by about 3-6 hours for the patients with depression, and delayed by about 6-12 hours for the patients with mixed mania.

Figure 3A:
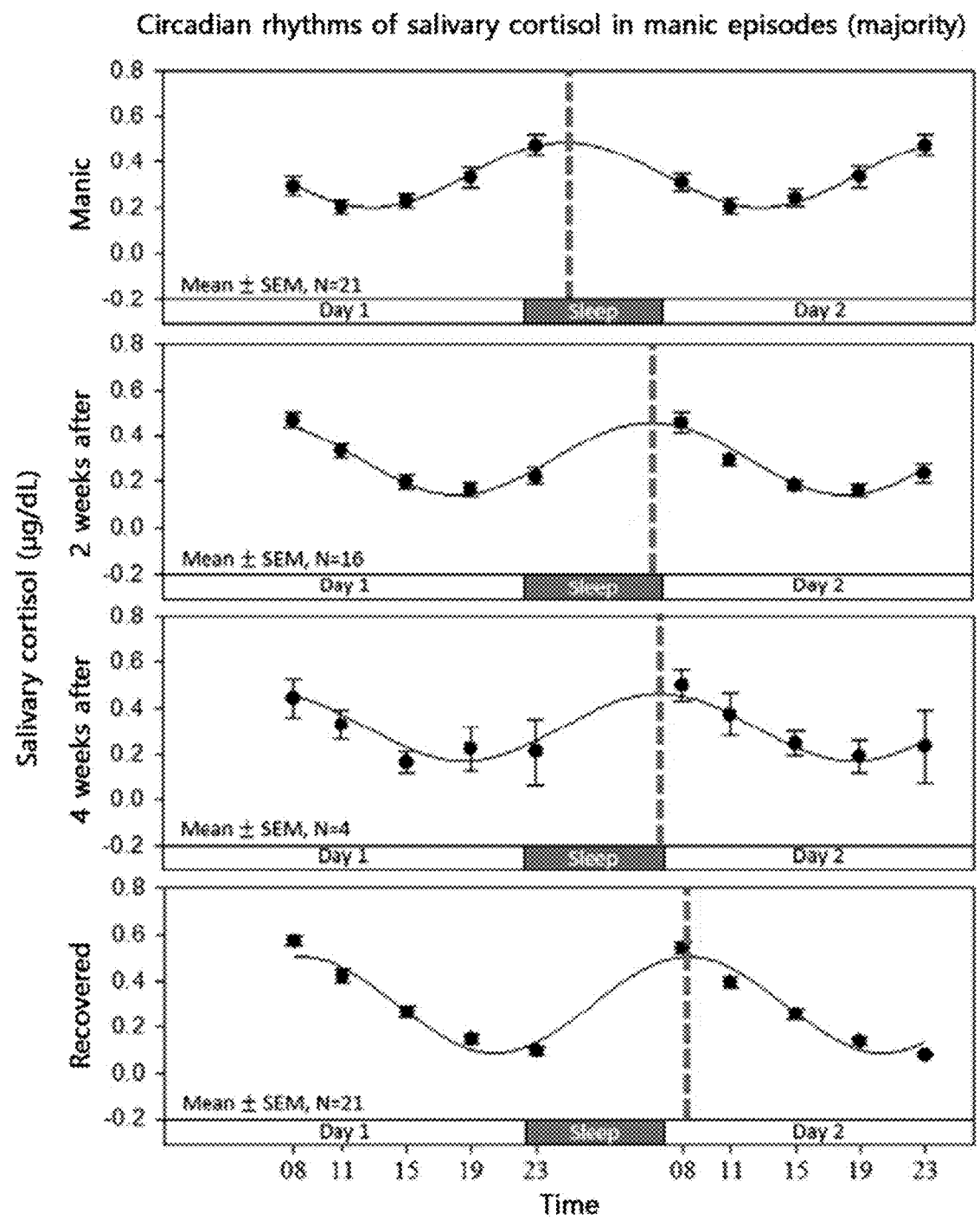
FIG. 3A is a graph showing the change in a circadian rhythm of cortisol for a patient with mania during treatment.
Figure 3B:
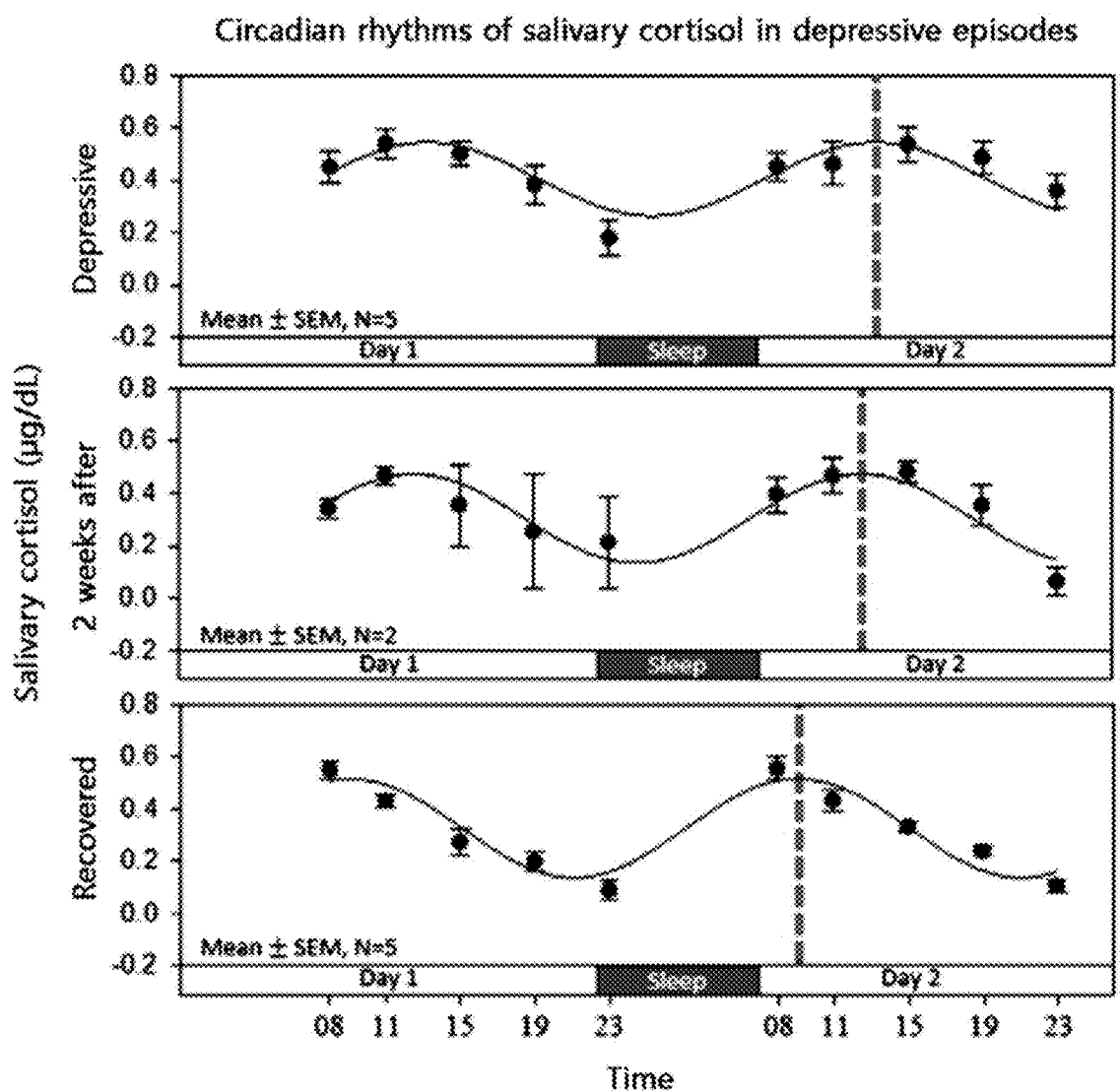
FIG. 3B is a graph showing the change in a circadian rhythm for a patient with depression during treatment.
Figure 3C:
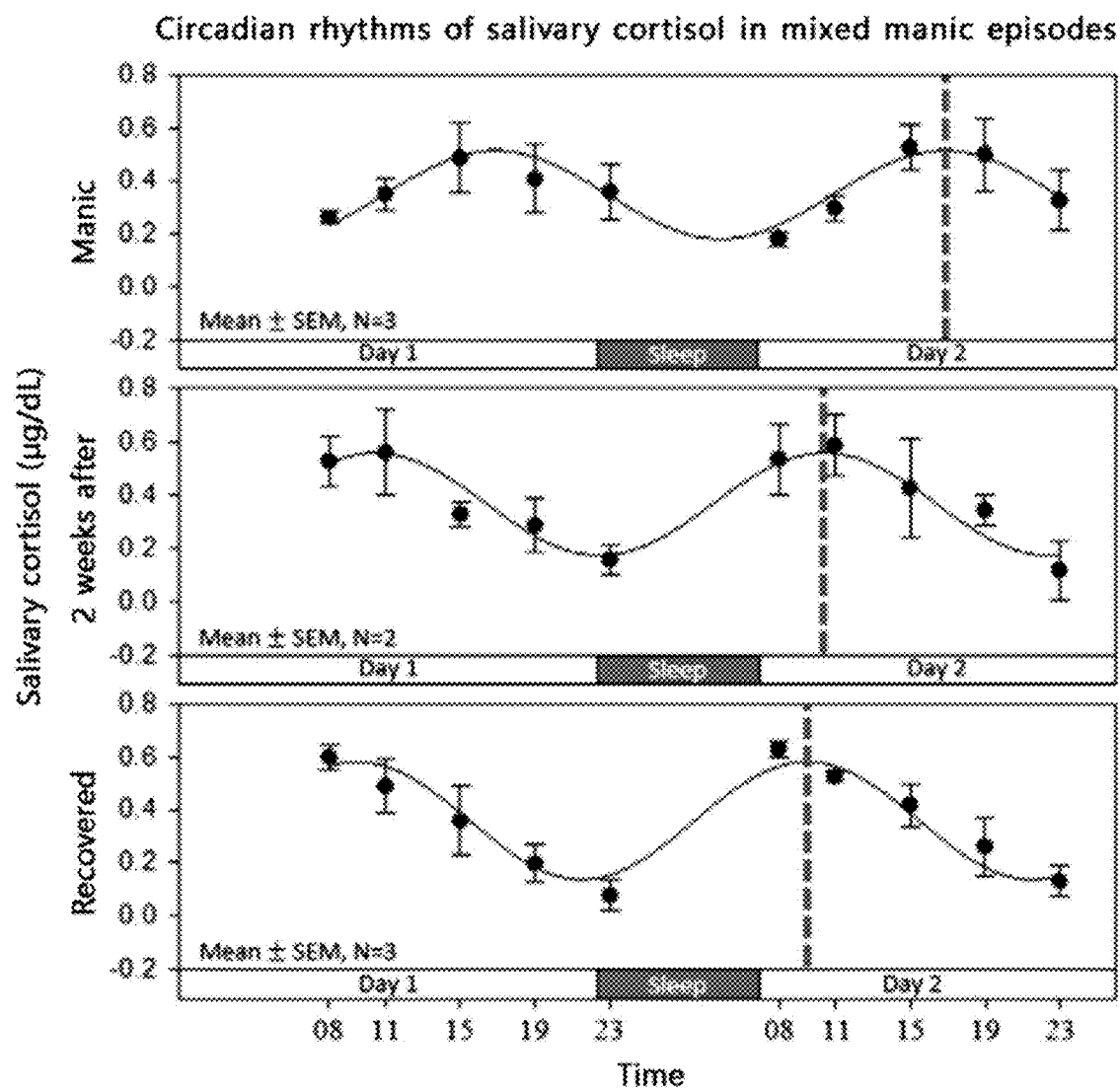
FIG. 3C is a graph showing the change in a circadian rhythm for a patient with mixed mania during treatment.

Meanwhile, FIG. 3A shows the change in the circadian rhythm during the treatment period of patients with mania, FIG. 3B shows the change in the circadian rhythm during the treatment period of patients with depression, and FIG. 3C shows the change in the circadian rhythm during the treatment period of patients with mixed mania.

As shown in the biochemical circadian rhythms of FIG. 2A and FIGS. 3A-3C, recovery from acute bipolar disorder was observed. When comparing the biochemical circadian rhythm of acute mood episode with the circadian rhythm of the recovered state, it can be seen that they commence with different phases.

Example 2: Diagnostic Method Using Circadian Rhythm (PER1/ARNTL Genes)

Through literature searches, 10 clock genes were selected as candidate genes (initial 10 candidate genes: ARNTL, PER1, PER2, PER3, NR1D1, NR1D2, CLOCK, CRY1, CRY2, NPAS2). Experiment was conducted for these 10 candidate genes, and 5 genes whose expression patterns could be observed clearly under the actual laboratory environment were chosen (5 chosen candidate genes: ARNTL, PER1, PER2, PER3, NR1D1).

In order to observe the circadian rhythms of gene expression, the five circadian clock genes (ARNTL, PER1, PER2, PER3, NR1D1) extracted from buccal epithelial cells were tested. After preparing samples by harvesting the buccal epithelial cells suspected with mental disorder for two days at 8:00, 11:00, 15:00, 19:00 and 23:00, for a total of 10 times, the RNAs of the five circadian clock genes (ARNTL, PER1, PER2, PER3, NR1D1) were extracted from the samples. DNAs were synthesized from the extracted RNAs, and the synthesized DNAs were amplified by real-time PCR to identify the circadian expression patterns. The circadian expression patterns of the circadian clock genes are shown in FIG. 4.

Figure 4:
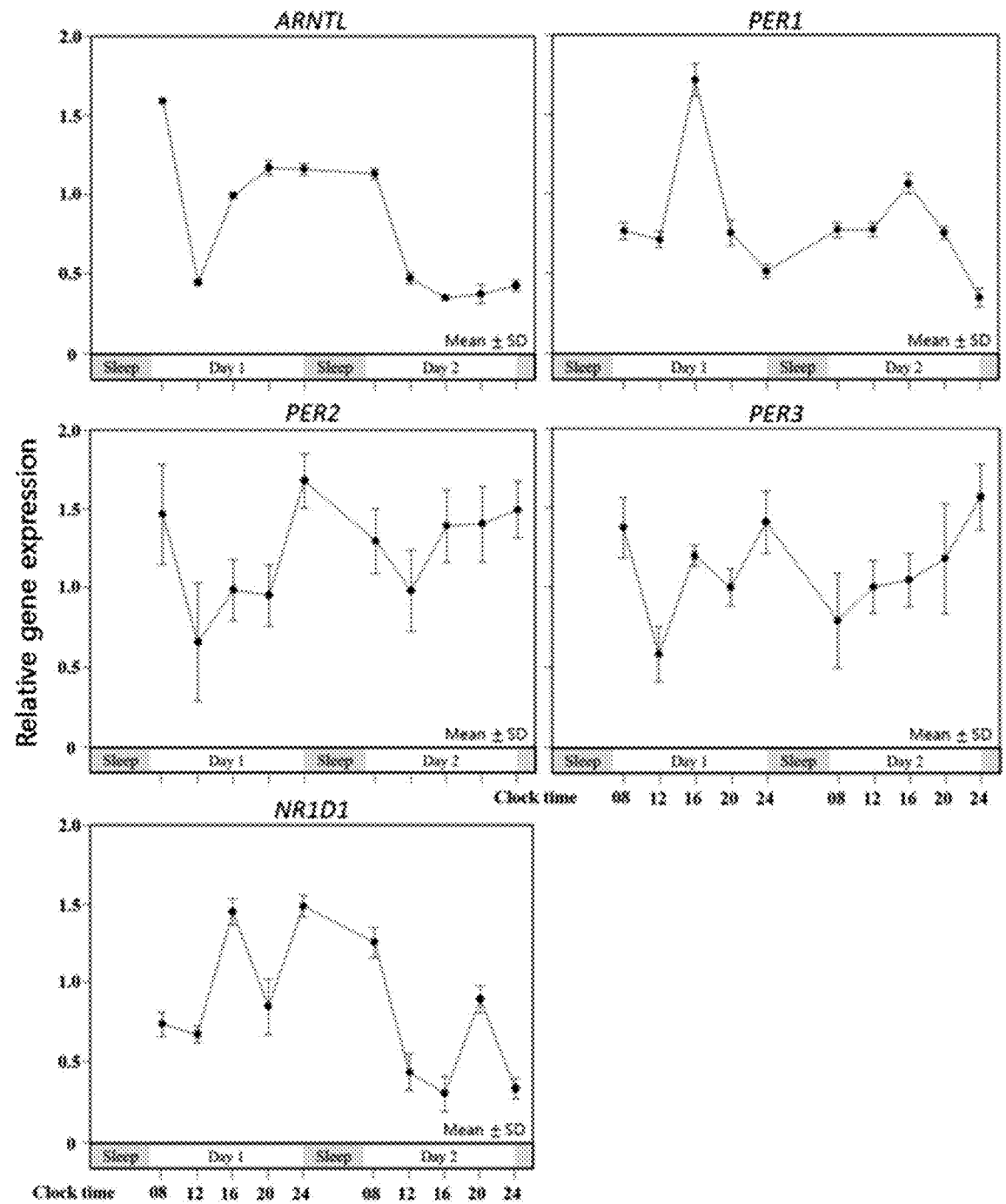
FIG. 4 shows graphs showing the circadian expression pattern of circadian clock genes (ARNTL, PER1, PER2, PER3, NR1D1).

As shown in FIG. 4, none of the expression patterns of the five genes showed a stable circadian rhythm. Although the five genes were amplified effectively by the real-time PCR technique with the expectation that expression patterns of the five genes would exhibit circadian rhythms, no stable circadian rhythm could be observed for the following reasons. (1) Because the present disclosure is directed to assisting in the diagnosis of the patients with mental disorder, samples were obtained in a non-invasive manner for clinical application without giving pain to the patients. That is to say, buccal epithelial cells were used as test samples, rather than blood. (2) Because the buccal epithelial cells vary depending on the circumstances within the oral cavity when they are sampled, it is impossible to taken an accurate amount. Therefore, the number of the cells varies, and so does the quantity of the genes measured. (3) In addition, the buccal epithelial cells are harvested inevitably together with saliva. Because saliva contains the enzymes that break down RNAs in order to protect the human body from viruses, the quantity of the extracted RNAs vary inevitably depending on the amount of the saliva taken together with the buccal epithelial cells despite the treatment with reagents to minimize RNA damage by saliva.

In order to solve this problem, a method of determining the circadian rhythm as a ratio of the expression levels of the two genes was devised. Although the number of cells used as samples is different and it is impossible to accurately determine the expression pattern of individual RNAs due to the enzymes in saliva, the ratio of the expression levels of the two genes can be measured accurately as if they were measured under the same conditions (the same number of cells and the same quantity of saliva). Paying attention to the fact that the circadian rhythms of the PER1 and ARNTL genes among the individual gene shown in FIG. 4 move in opposite directions, the ratio of the expression levels of the two genes were calculated to maximize their patterns. The result is shown in FIG. 5.

Figure 5:
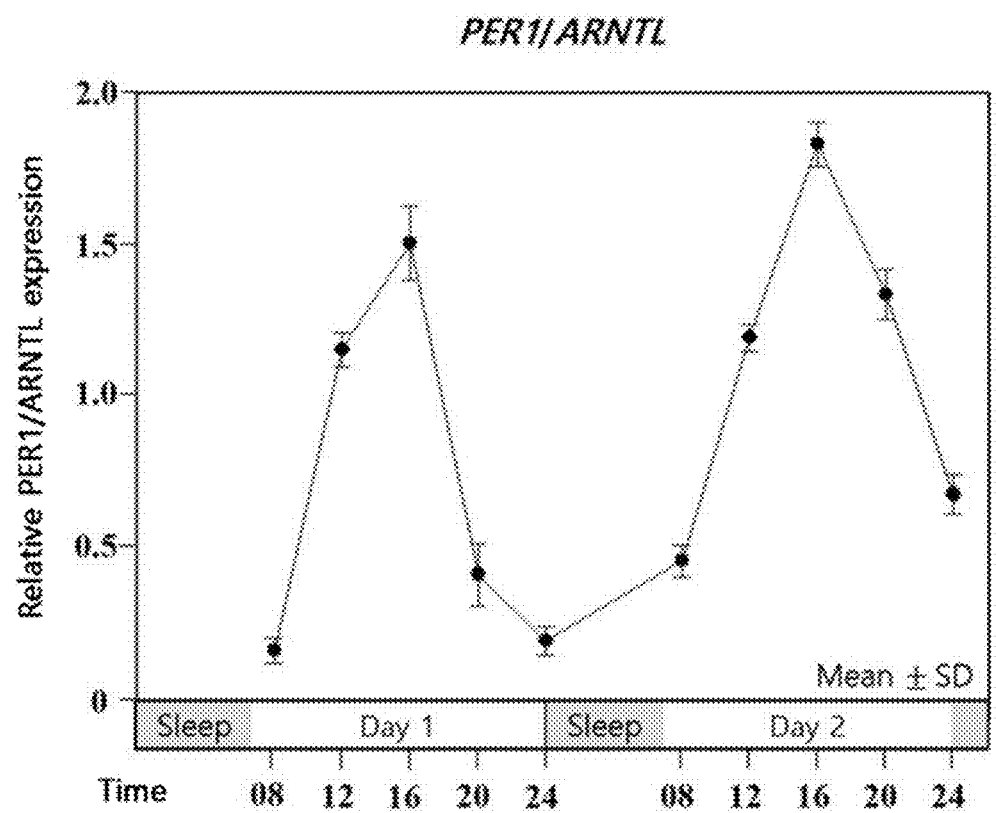
FIG. 5 is a graph showing a result of maximizing a circadian rhythm by calculating a ratio the expression levels of the PER1/ARNTL genes.

As shown in FIG. 5, it was confirmed that the biological circadian rhythm represented by the ratio of the expression levels of the PER1 and ARNTL genes appears stable. That is, it was confirmed that the ARNTL and PER1 genes are more appropriate to measure the circadian rhythm than other genes.

The circadian rhythms of the ARNTL and PER1 genes were in agreement with previous studies of circadian oscillation (Akashi et al., 2010, Chung et al., 2014, Guo et al., 2006, Novakova et al. 2015, Son et al., 2008) and were inverse in phase to each other. Accordingly, to obtain the most distinguishable circadian rhythms, the relative gene expression of ARNTL and PER1 was investigated, as performed and verified in previous studies (Cho et al., 2016; Guo et al., 2006).

First, total RNAs were isolated from the buccal epithelial cells using the RNeasy Micro Kit (Qiagen Inc., Valencia, Calif., USA), and only RNA samples concentrated to >200 ng/µL were subjected to the next steps. The RNA samples were reverse-transcribed using the Sensiscript Reverse Transcription Kit (Qiagen). Then, cDNAs were subjected to the Taqman PCR reaction using the Applied Biosystems StepOnePlus Real-Time PCR Systems (ThermoFisher Scientific, Foster City, Calif., USA). The primers and Taqman probes used in this experiment are as follows.

```
                                          (SEQ ID NO: 1)
PER1 (NM_002616): forward 5'-CTCACACAGCT    reverse
CCTCCTCAG-3', (SEQ ID NO: 2)
5'-TTTGTGCTCTTGCTGCTCTC-3',                   probe (SEQ ID NO: 3)
5'FAM-CGGCAAGGACTCAGCCCTGC-3'BHQ1;

(SEQ ID NO: 4)
ARNTL (NM_001030272): forward 5'-TGCCTCGT   reverse
CGCAATTGG-3', (SEQ ID NO: 5)
5'-ACCCTGATTTCCCCGTTCA-3',                    probe (SEQ ID NO: 6)
5'FAM-CGACTGCATTCTCATGTAGTTCCACAACCA-
3'BHQ1.
```

In short, the circadian gene expression levels of PER1 and ARNTL were determined by RT-qPCR. The ratio of the expression levels of the PER1/ARNTL genes at each sampling time was calculated and acquired as time-series data, and the optimized circadian rhythm in the form of a sine curve was embodied. The SigmaPlot software (Systat Software Inc., San Jose, Calif., USA) was used to embody the biochemical circadian rhythm as the sine curve.

Figure 1B:
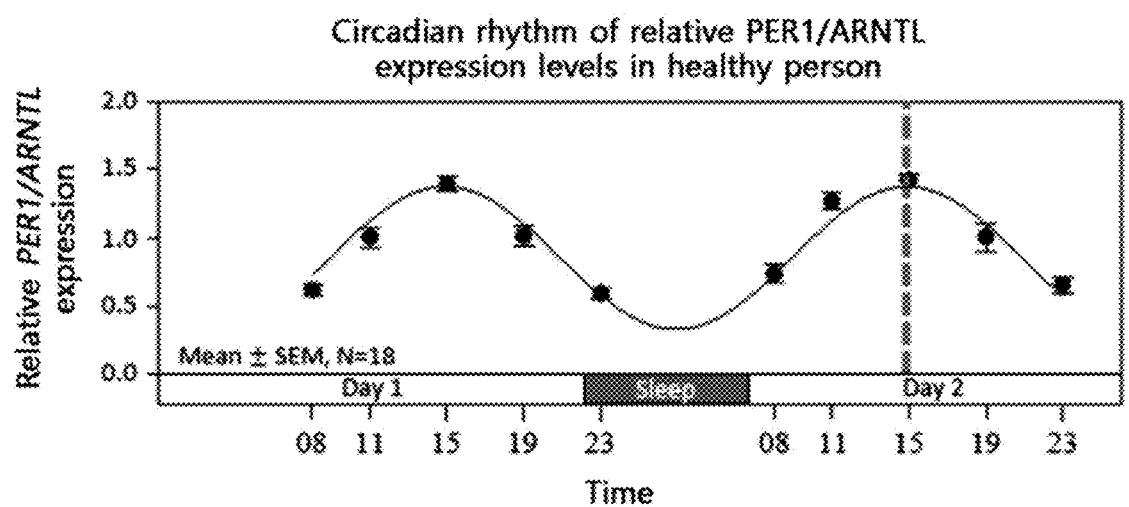
FIG. 1B is a graph showing the circadian rhythm of a normal person embodied by calculating a ratio of the expression levels the PER1 gene and the ARNTL gene.

The embodied circadian rhythm of the patient was compared with the circadian rhythm of a normal person shown in FIG. 1B. Mania was diagnosed if the circadian rhythm was 4-12 ahead as compared to a normal person, depression was diagnosed if the circadian rhythm was delayed by 3-6 hours as compared to a normal person, and mixed mania was diagnosed if the circadian rhythm was delayed by 6-12 hours as compared to a normal person.

Then, the patients diagnosed with mood disorder were monitored while treating for 2-4 weeks.

Figure 2B:
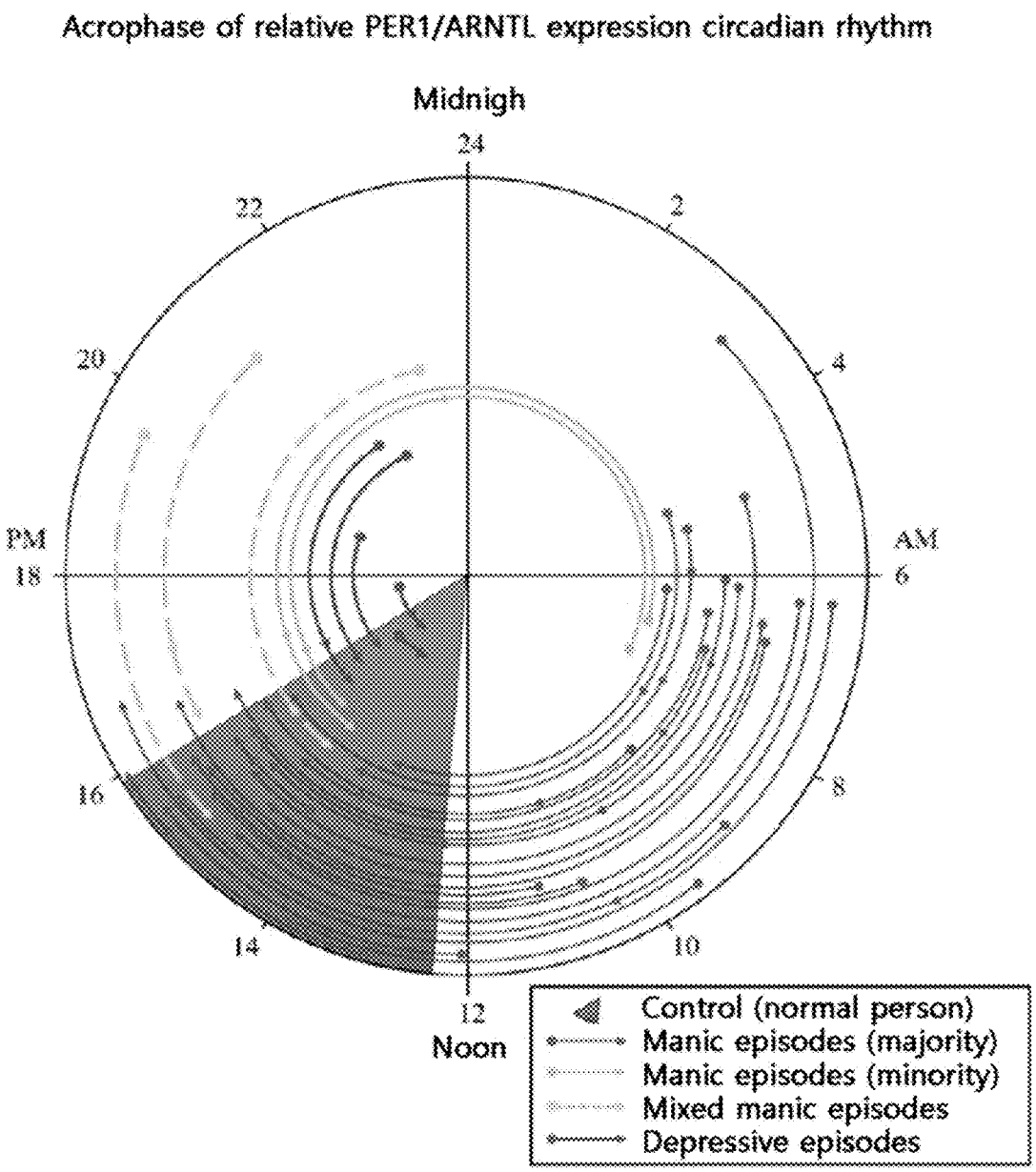
FIG. 2B is a diagram showing the change in the acrophase of a biochemical circadian rhythm of a ratio of the expression levels of the PER1/ARNTL genes for mania and depressive episode during treatment.

FIG. 2B and Tables 3-4 clearly show that the biochemical circadian rhythms of acute mania and depressive episode are different from the biochemical circadian rhythm of the control group (normal). In particular, as shown in FIG. 2B, although the biochemical circadian rhythms had contrasting initial phases during acute mania and depression, they were transited by comparable phase shifts during recovery, almost entirely arriving within the normal ranges.

TABLE 3

| | Manic episodes (N = 26) | | | | | | | |
|---|---|---|---|---|---|---|---|---|
| | Manic episodes (majority) | | | | Manic episodes (minority) | | | |
| Observation | Mania N = 21 | 2 weeks after N = 16 | 4 weeks after N = 4 | Recovered N = 21 | Mania N = 2 | 2 weeks after N = 2 | 4 weeks after N = 2 | Recovered N = 2 |
| Acrophase (h) | 7.78 ± 2.92 | 11.85 ± 2.95 | 12.17 ± 3.24 | 15.34 ± 0.81 | 7.21 ± 0.75 | 22.05 ± 2.24 | 16.57 ± 0.15 | 14.66 ± 0.75 |
| Amplitude | 19.24 ± 8.15 | 20.1 ± 5.62 | 24.07 ± 3.03 | 27.26 ± 4.74 | 21.03 ± 5.41 | 22.61 ± 3.24 | 26.57 ± 9.26 | 22.03 ± 10.92 |

N: number of episodes in bipolar disorder patients

TABLE 4

| | Manic episodes (N = 26) Mixed manic episodes | | | Depressive episodes | | | Controls |
|---|---|---|---|---|---|---|---|
| Observation | Mixed N = 3 | 2 weeks after N = 2 | Recovered N = 3 | Depressive N = 5 | 2 weeks after N = 2 | Recovered N = 5 | (normal people) N = 18 |
| Acrophase (h) | 21.41 ± 1.77 | 16.40 ± 1.12 | 14.97 ± 1.01 | 19.21 ± 2.87 | 15.38 ± 0.77 | 14.82 ± 0.57 | 14.85 ± 0.76 |
| Amplitude | 17.95 ± 7.33 | 25.60 ± 0.47 | 24.14 ± 5.97 | 19.41 ± 10.07 | 19.78 ± 9.71 | 25.83 ± 6.78 | 26.58 ± 5.17 |

N: number of episodes in bipolar disorder patients or number or people in control group (normal)

As shown in Table 3 and Table 4, the circadian rhythm or acrophase of manic patients were 4-12 hours ahead as compared to the normal people. It was delayed by about 3-6 hours for the patients with depression, and delayed by about 6-12 hours for the patients with mixed mania.

Figure 6A:
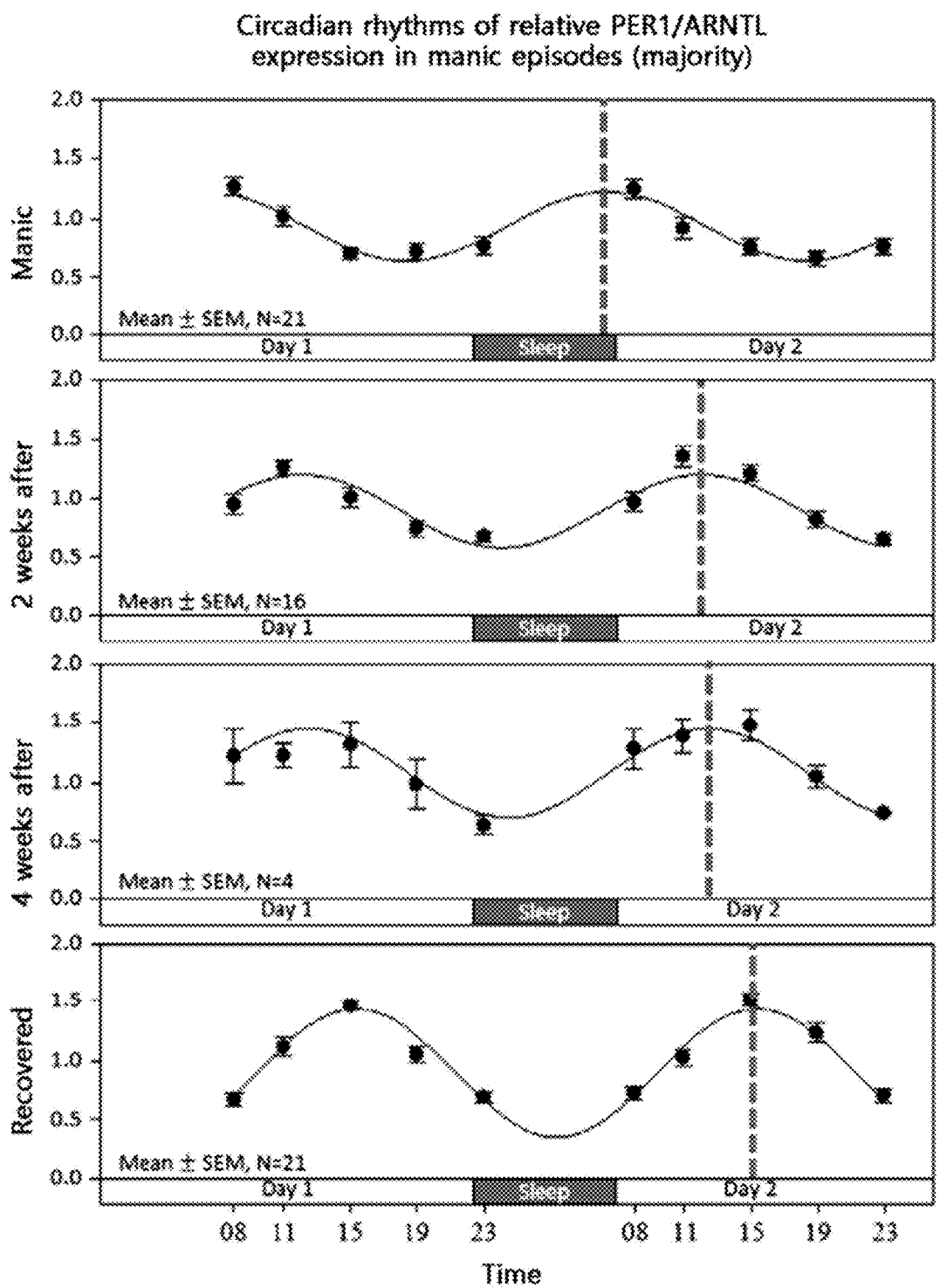
FIG. 6A is a graph showing the change in a circadian rhythm of a ratio the expression levels of the PER1/ARNTL genes for a patient with mania during treatment.
Figure 6B:
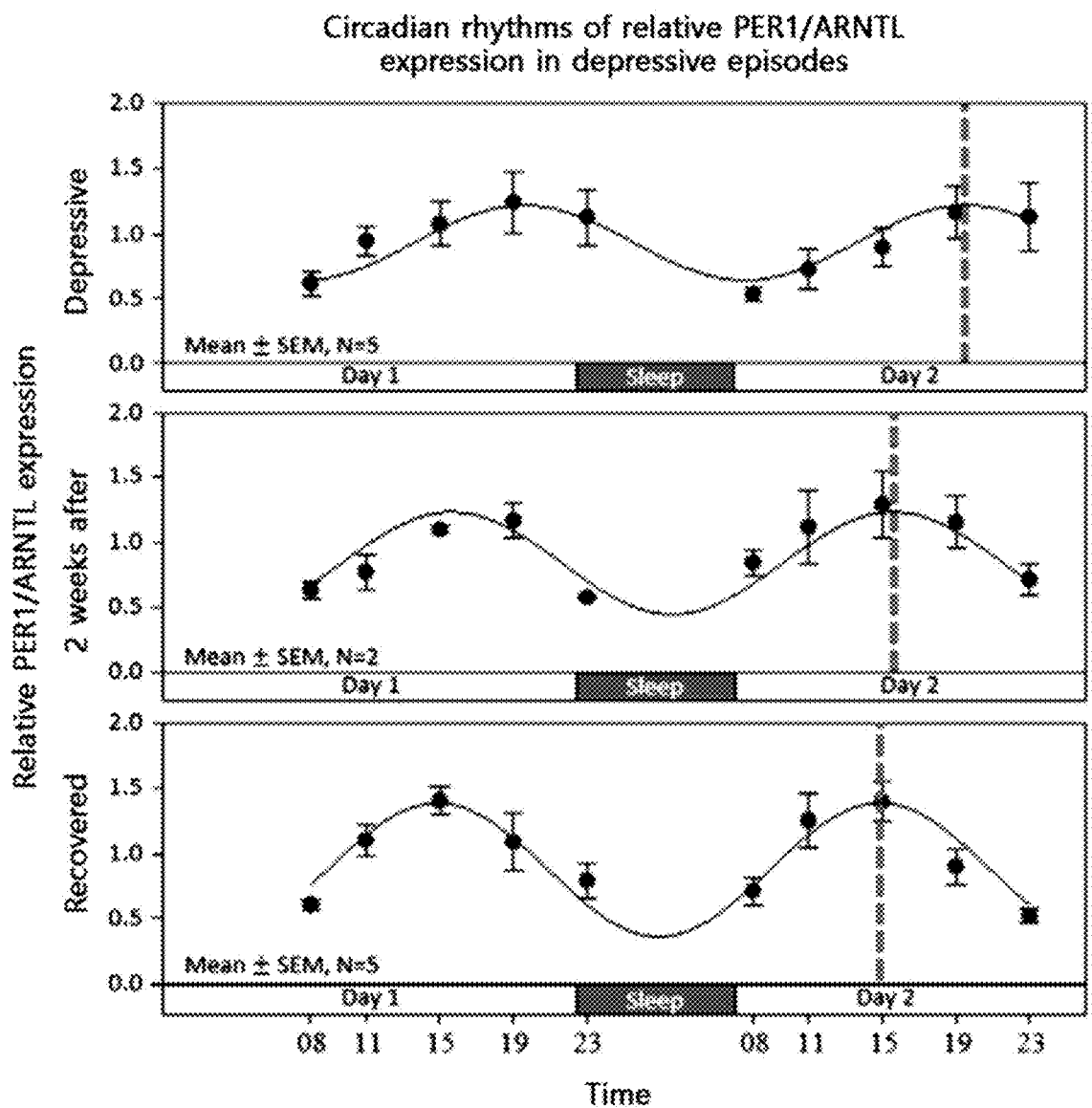
FIG. 6B is a graph showing the change in a circadian rhythm for a patient with depression during treatment.
Figure 6C:
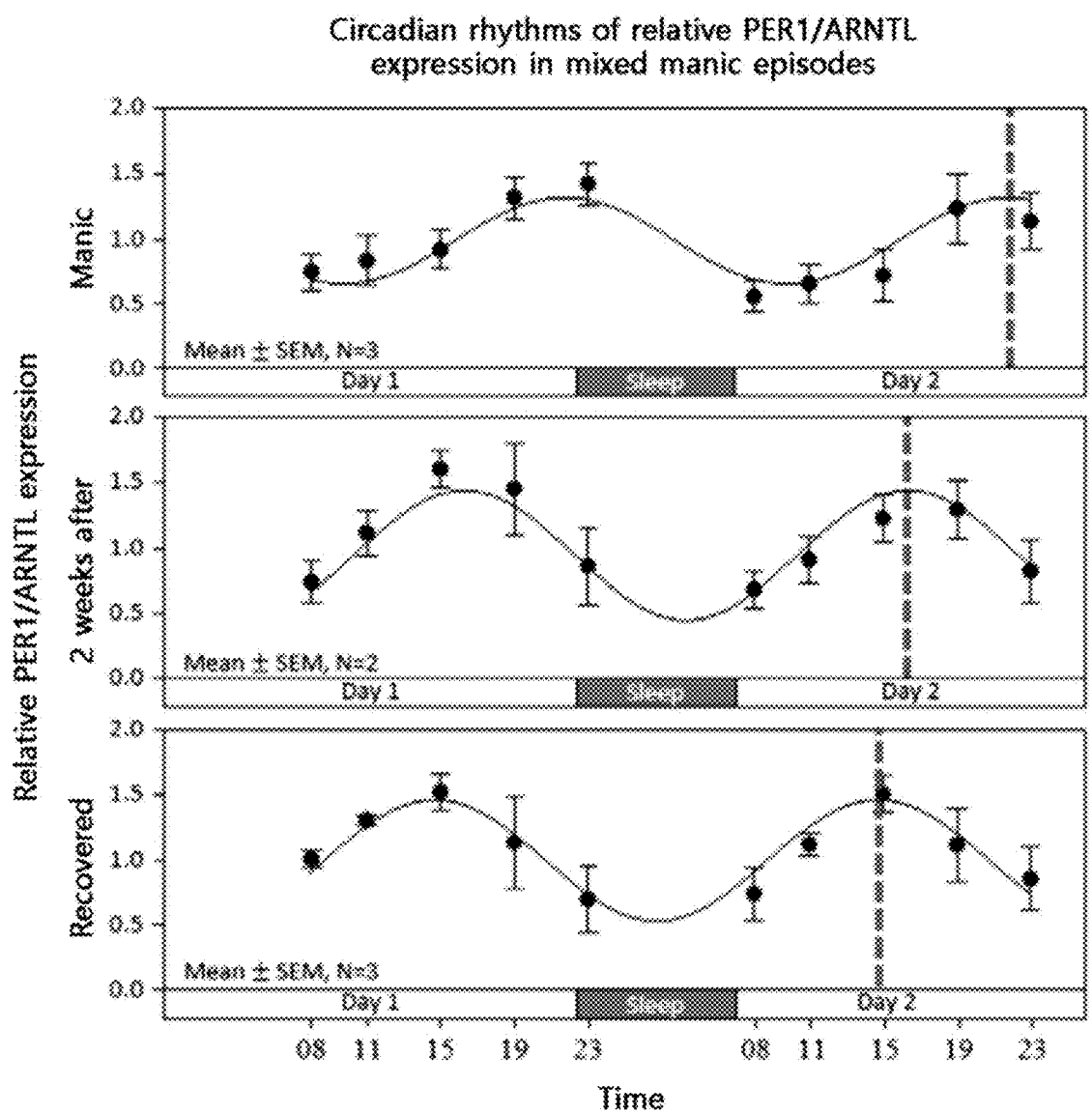
FIG. 6C is a graph showing the change in a circadian rhythm for a patient with mixed mania during treatment.

Meanwhile, FIG. 6A is a graph showing the change in the circadian rhythm for patients with mania during treatment, FIG. 6B is a graph showing the change in the circadian rhythm for patients with depression during treatment, and FIG. 6C is a graph showing the change in the circadian rhythm for patients with mixed mania during treatment.

As shown in the graphs of FIG. 2B and FIGS. 6A to 6C, the change in the biochemical circadian rhythm of recovery from acute bipolar disorder was observed. When comparing the biochemical circadian rhythm of acute mood episode with the circadian rhythm of the recovered state, it can be seen that they commence with different phases.

Figure 7:
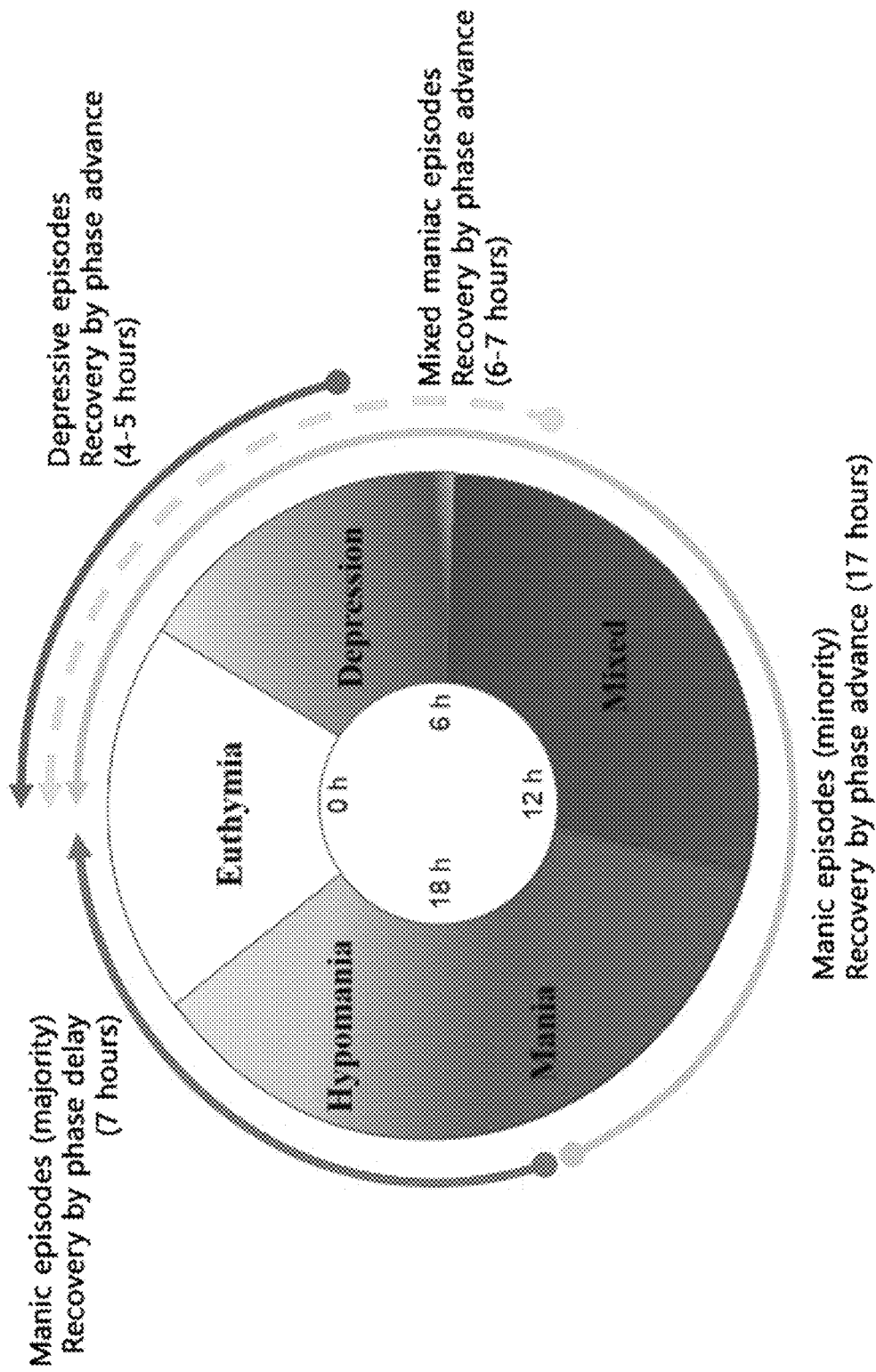
FIG. 7 is a schematic diagram showing a circadian rhythm change model for mood disorder such as mania, depression, mixed mania, etc.

The hypothesis on the circadian rhythm change model of bipolar disorder based on Example 1 and Example 2 is schematically illustrated in FIG. 7. FIG. 7 shows that circadian phase orientations had distinct abnormalities in acute manic episodes versus mixed episodes versus depressive episodes. The phase disturbance is resolved through advance or delay to recover the normal phase orientation after treatment.

The invention claimed is:

1. A method of diagnosing mania, depression and mixed mania using the change of a circadian rhythm and treatment thereof, comprising the steps of:
   determining an acrophase in a circadian rhythm of a subject comprising the steps of:
   collecting a biological sample from the subject for 24-48 hours with an interval of 2-6 hours, wherein the biological sample is saliva;
   measuring concentration of cortisol within the biological sample of the subject; and
   embodying the circadian rhythm of the subject as an optimized sine function by acquiring the measured concentration of cortisol as time-series data;
   wherein the acrophase is a time when the circadian rhythm of the subject as the optimized sine function reaches a maximum peak;
   determining an acrophase in a circadian rhythm of a normal person comprising the steps of:
   collecting a biological sample from the normal person for 24-48 hours with an interval of 2-6 hours, wherein the biological sample is saliva;
   measuring concentration of cortisol within the biological sample of the normal person; and
   embodying the circadian rhythm of the normal person as an optimized sine function by acquiring the measured concentration of cortisol as time-series data;
   wherein the acrophase is a time when the circadian rhythm of the normal person as the optimized sine function reaches a maximum peak;
   comparing the acrophase of the circadian rhythm of the subject with the acrophase of the circadian rhythm of the normal person to determine whether the circadian rhythm of the subject is ahead or delayed compared to that of the normal person; and
   diagnosing the subject with mania if the circadian rhythm of the subject is 4-12 hours ahead as compared to the circadian rhythm of the normal person;
   diagnosing the subject with depression if the circadian rhythm of the subject is delayed by 3-6 hours as compared to the circadian rhythm of the normal person;
   diagnosing the subject with mixed mania if the circadian rhythm of the subject is delayed by 6-12 hours as compared to the circadian rhythm of the normal person; and
   treating the subject diagnosed with mania, depression, or mixed mania for 2-4 weeks comprising resetting the subject's circadian rhythm;
   wherein resetting the subject's circadian rhythm in treating mania comprises delaying the circadian rhythm by 4-12 hours;
   wherein resetting the subject's circadian rhythm in treating depression comprises advancing the circadian rhythm by 3-6 hours,
   wherein resetting the subject's circadian rhythm in treating mixed mania comprises advancing the circadian rhythm by 6-12 hours; and
   wherein delaying or advancing the circadian rhythm comprises controlling the subject's sleep habits;
   wherein controlling the subject's sleep habits comprises sleeping during set sleeping hours and restricting the subject's exposure to light during the set sleeping hours.

2. The method of diagnosing mania, depression and mixed mania according to claim 1, wherein measurement of the cortisol concentration excludes the set sleeping hours.

3. The method of claim 1, wherein treating further comprises exposing the subject to natural light outside of the set sleeping hours.

4. A method of diagnosing mania, depression and mixed mania using the change of a circadian rhythm and treatment thereof, comprising the steps of:
   determining an acrophase in a circadian rhythm of a subject comprising the steps of:
   collecting a biological sample from the subject for 24-48 hours with an interval of 2-6 hours, wherein the biological sample is buccal epithelial cells;
   measuring expression levels of PER1 gene and ARNTL gene of the subject within the biological sample of the subject;
   calculating a value from the expression levels of the PER1 gene and the ARNTL gene of the subject obtained by dividing the measured expression level of the PER1 gene by the measured expression level of the ARNTL gene; and
   embodying the circadian rhythm of the subject as an optimized sine function by acquiring the measured expression levels of PER1 gene and ARNTL gene of the subject as time-series data;
   wherein the acrophase is a time when the circadian rhythm of the subject as the optimized sine function reaches a maximum peak;
   determining an acrophase in a circadian rhythm of a normal person comprising the steps of:
   collecting a biological sample from the normal person for 24-48 hours with an interval of 2-6 hours, wherein the biological sample is buccal epithelial cells;

measuring expression levels of PER1 gene and ARNTL gene of the normal person within the biological sample of the normal person;

calculating a value from the expression levels of the PER1 gene and the ARNTL gene of the normal person obtained by dividing the measured expression level of the PER1 gene by the measured expression level of the ARNTL gene; and embodying the circadian rhythm of the normal person as an optimized sine function by acquiring the measured expression levels of PER1 gene and ARNTL gene of the normal person as time-series data;

wherein the acrophase is a time when the circadian rhythm of the normal person as the optimized sine function reaches a maximum peak;

comparing the acrophase of the circadian rhythm of the subject with the acrophase of the circadian rhythm of the normal person to determine whether the circadian rhythm of the subject is ahead or delayed compared to that of the normal person; and diagnosing the subject with mania if the circadian rhythm of the subject is 4-12 hours ahead as compared to the circadian rhythm of the normal person;

diagnosing the subject with depression if the circadian rhythm of the subject is delayed by 3-6 hours as compared to the circadian rhythm of the normal person;

diagnosing the subject with mixed mania if the circadian rhythm of the subject is delayed by 6-12 hours as compared to the circadian rhythm of the normal person; and treating the subject diagnosed with mania, depression, or mixed mania for 2-4 weeks comprising resetting the subject's circadian rhythm;

wherein resetting the subject's circadian rhythm in treating mania comprises delaying the circadian rhythm by 4-12 hours;

wherein resetting the subject's circadian rhythm in treating depression comprises advancing the circadian rhythm by 3-6 hours, wherein resetting the subject's circadian rhythm in treating mixed mania comprises advancing the circadian rhythm by 6-12 hours; and wherein delaying or advancing the circadian rhythm comprises controlling the subject's sleep habits;

wherein controlling the subject's sleep habits comprises sleeping during set sleeping hours and restricting the subject's exposure to light during the set sleeping hours.

5. The method of diagnosing mania, depression and mixed mania according to claim 4, wherein measurement of the PER1 gene and the ARNTL gene expression levels excludes the set sleeping hours.

6. The method of claim 4, wherein treating further comprises exposing the subject to natural light outside of the set sleeping hours.

* * * * *